US00PP37533P2

(12) United States Plant Patent
Korlipara

(10) Patent No.: US PP37,533 P2
(45) Date of Patent: Jul. 21, 2026

(54) ***ECHINACEA* PLANT NAMED 'Fried Egg'**

(50) Latin Name: ***Echinacea* spp.**
Varietal Denomination: Fried Egg

(71) Applicant: Terra Nova Nurseries, Inc., Canby, OR (US)

(72) Inventor: Harini Korlipara, Tualatin, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 19/380,455

(22) Filed: Nov. 5, 2025

(51) Int. Cl.
*A01H 5/02* (2018.01)
*A01H 6/14* (2018.01)

(52) U.S. Cl.
USPC ..... Plt./428

(58) Field of Classification Search
USPC ..... Plt./428
See application file for complete search history.

(56) References Cited

U.S. PATENT DOCUMENTS

PP24,506 P2 * 5/2014 Korlipara ..... A01H 6/14
Plt./428

* cited by examiner

*Primary Examiner* — Susan Mccormick Ewoldt
*Assistant Examiner* — Zachariah Allan Kay
(74) *Attorney, Agent, or Firm* — Klarquist Sparkman, LLP

(57) ABSTRACT

A new and distinct *Echinacea* plant variety named 'Fried Egg' is disclosed, characterized by white ray petals and yellow disc petals, mature flowers that can uniformly fade to greyed yellow, and a strong pleasant honey-like scent.

2 Drawing Sheets

Latin name of the genus and species of the plant claimed: *Echinacea* spp.

Variety denomination: 'Fried Egg'.

BACKGROUND

The present application relates to a new and distinct cultivar of *Echinacea* named 'Fried Egg'. *Echinacea* is in the family Asteraceae. The new cultivar 'Fried Egg' originated as a part of a planned breeding program to produce compact well crowning plants with double inflorescences.

SUMMARY

The new plant resulted from a cross of seed donor (female) parent E2111 (unpatented) and pollen donor (male) parent E2052 (unpatented). Both parents are unnamed and undescribed proprietary interspecific hybrids bred from *Echinacea paradoxa, Echinacea purpurea*, and *Echinacea tennesseensis*. The new cultivar, 'Fried Egg', was selected when growing in a cultivated area in Canby, Oregon.

'Fried Egg' is distinguished from other *Echinacea* varieties at least due to the following unique combination of characteristics:

1. Disc petals that are a different color from the ray petals
2. Flowers can fade uniformly to greyed yellow as they mature
3. Very strong pleasant honey-like scent The new variety is distinct from other known *Echinacea* varieties, for example, compared to CARA MIA® 'Sands' (unpatented), 'Fried Egg' has disc petals that are a different color than the ray petals upon maturity, has ray petals that become greyed yellow instead of white as the flower matures, and has a more compact habit. Compared to DELIGHTFUL™ 'Gold' (unpatented), 'Fried Egg' has disc flowers that are a different color than its ray petals upon maturity, has disc petals that are white instead of yellow, and has a larger overall habit.

The new cultivar has been reproduced by asexual propagation. Each of the progeny exhibit identical characteristics to the original plant. Asexual propagation by cuttings and tissue culture using standard micropropagation techniques with terminal and lateral shoots, as done in Canby, Oregon, shows that the characteristics described herein come true to form, are firmly fixed, and are established and transmitted through succeeding propagations.

Figure 1:
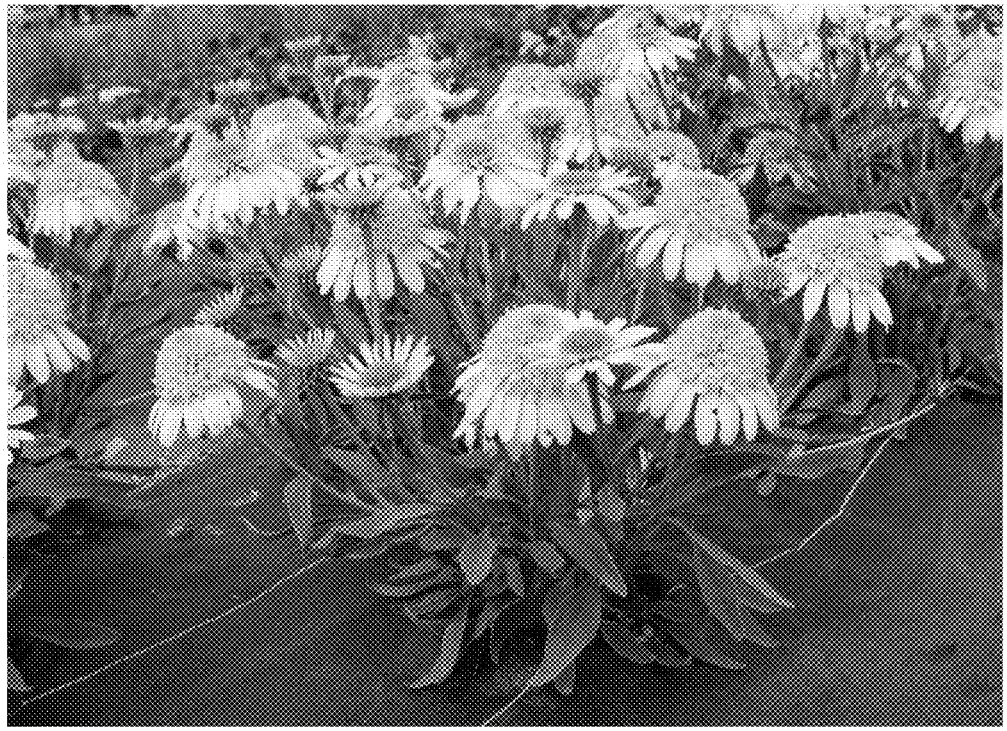
FIG. 1 shows a 20-month-old plant that was field grown in full sun in Canby, OR. The photograph was taken in August 2024.
Figure 2:
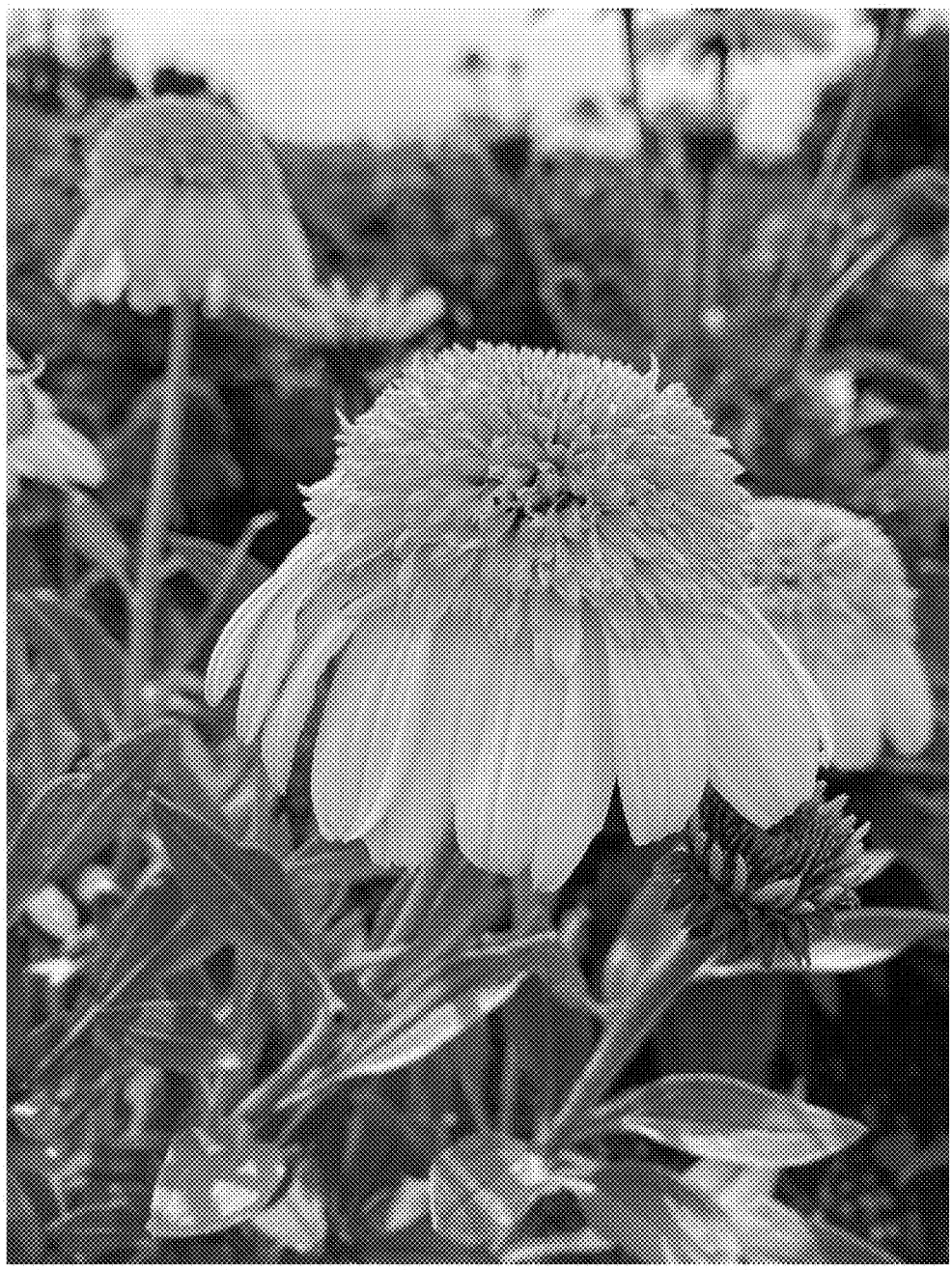
FIG. 2 shows a close-up of a bloom on a 20-month-old plant that was field grown in full sun in Canby, OR. The photograph was taken in August of 2023.

The color photographs show typical specimens of the new variety and depict the color as nearly true as is reasonably possible to make the same in a color illustration of this character. It should be noted that colors may vary, for example due to lighting conditions at the time the photograph is taken. Therefore, color characteristics of this new variety should be determined with reference to the observations described herein, rather than from the photographs alone.

DETAILED DESCRIPTION

The following is a detailed description of the new *Echinacea* cultivar based on observations taken in the month of August of a 25-month-old asexually reproduced progeny grown in full sun in field conditions in Canby, Oregon. Canby is Zone 8 on the USDA Hardiness map. Temperatures range from a high of 95° F. in August to an average of 32° F. in January. Normal rainfall in Canby is 42.8 inches per year.

Certain characteristics of this variety may change with changing environmental conditions (such as photoperiod, temperature, moisture, soil conditions, nutrient availability, or other factors) without a change in genotype. Color descriptions and other terminology are used in accordance with their ordinary dictionary descriptions, unless the context clearly indicates otherwise. Color designations (hue/value/chroma) are made with reference to The Royal Horticultural Society Colour Chart (R.H.S.), 5$^{th}$ edition, London, England, 2007.

Parentage:

*Female parent*.—E2111 (unpatented).

*Male parent*.—E2052 (unpatented).

Plant:

*Type*.—Herbaceous perennial.

*Hardiness*.—USDA zones 4-9.

*Size*.—40-60 cm wide and 35-50 cm tall to top of inflorescence.

*Form/growth habit*.—Basal clump.

*Vigor*.—Good.

Number of crowns.—7-12 stems from the base.

Roots:

*Color*.—Overall, RHS 157D.

*Description*.—Fibrous with many downward growing roots with few lateral roots.

Stem (flowering):

*Type*.—Ascending with 1-8 inflorescences per stem.

*Size*.—Up to 50 cm tall at terminal inflorescence, up to 9 mm wide at base.

*Strength*.—Strong.

*Internode length*.—1.5-8.0 cm.

*Surface texture*.—Strigose.

*Rugosity*.—Weak.

*Variegation*.—Absent.

*Color*.—RHS 145A speckled with RHS 143B.

Leaves (stem):

*Type*.—Simple.

*Shape*.—Lanceolate.

*Arrangement*.—Alternate.

*Blade size*.—Length: 5-9 cm. Width: 1-3 cm.

*Margins*.—Entire, strigose.

*Apex*.—Acute.

*Base*.—Attenuate.

*Surface texture top*.—Strigose, weak to medium rugosity.

*Surface texture bottom*.—Strigose.

*Venation*.—Pinnate.

*Vein color top*.—RHS N144D.

*Vein color bottom*.—RHS 145C.

*Leaf color*.—Immature Leaf: Upper Surface: Closest to RHS 146A. Lower Surface: RHS 146B. Mature Leaf: Upper Surface: RHS N137B. Lower Surface: RHS 146B.

*Lobing/division*.—Entire.

*Undulation*.—None to minor.

*Glossiness*.—Absent.

*Leaf rugosity*.—Weak to moderate.

*Petiole description on average full grown leaf*.—Color: On topside center colored RHS 144D and wings colored RHS 137B. Length: Approximately 4 cm. Width: Approximately 5 mm. Winged and keeled with strigose margins.

Leaves:

*Type*.—Simple.

*Shape*.—Lanceolate.

*Arrangement*.—Rosette.

*Blade size*.—Length: 10-12 cm. Width: 1.5-3.0 cm.

*Margins*.—Entire, slightly undulate, minorly dentate.

*Apex*.—Acute.

*Base*.—Attenuate.

*Surface texture top*.—Strigose, scaberulose.

*Surface texture bottom*.—Strigose, scaberulose.

*Venation*.—Pinnate.

*Vein color top*.—RHS 145C.

*Vein color bottom*.—RHS 145C.

*Leaf color*.—Immature Leaf: Upper Surface: Closest to RHS 146A. Lower Surface: RHS 146B. Mature Leaf: Upper Surface: RHS 147A. Lower Surface: RHS 147B.

*Lobing/division*.—Simple.

*Undulation*.—Minor.

*Glossiness*.—None.

*Leaf rugosity*.—Weak to moderate.

*Petiole description*.—Color: Closest to RHS 146C. Length: 8-10 cm. Width: 2-7 mm. Texture: Keeled and partially to entirely winged.

Inflorescence:

*Flowering stem*.—Height: 30-50 cm. Unbranched to branched with 1-9 inflorescences per stem. Size: Grows to 10 cm wide and 5 cm deep as disc enlarges.

*Type*.—Composite on terminal stalked heads.

*Size*.—Grows to 10 cm wide and 5 cm deep as disc enlarges.

*Form*.—Ray Florets: Present. Reflexing Present: Yes, downward. Mature Disc Shape: Conical.

*Immature inflorescence* (*bud*).—Width: 2.0 cm. Depth: 1.5 cm. Ray florets held at 90 degrees upright from vertical. Rolled (Only Back Color Shows): True, back color is closest to RHS 146D. Ray Color: RHS 1D. Ray Tip Color: RHS N144B. Disc Color: (Immature palea) RHS 144A.

*Ray florets*.—Pistil or Stamen: Not present. Number of Ray Florets: Approximately 15-25. Full Size Ray Floret Length: 4-6 cm. Full Size Ray Floret Width: 9-14 mm. Full Size Ray Floret Shape: Oblanceolate. Full Size Ray Floret Tip Description: Acuminate to 3 toothed.

*Margins*.—Entire.

*Base*.—Attenuate.

*Surface texture*.—Smooth.

*Immature fully opened floret colors*.—Topside: RHS 8D, teeth RHS 13B, base RHS N144D. Bottom Side: RHS 14D, teeth RHS 13A, base RHS 144D.

*Mature florets colors*.—Topside: RHS 160D, base closest to RHS 144D, teeth group RHS 12A. Bottom Side: RHS 160A streaked with RHS 144B, teeth RHS 12A, base RHS 145A.

*Pedicel*.—5 mm long, 2 mm wide; pedicel color RHS 155A; 5 fused sepals colored RHS 144C.

Disc:

*Shape*.—Flat becoming conic.

*Size*.—Becoming 5 cm deep and 6 cm wide with maturity.

*Color*.—Overall closest to RHS 11A.

*Disc florets*.—Number: Approximately 400-450, each with 1 pistil and 5 stamens. Floret Length: 2.0-2.5 cm. Floret Width: 4-9 mm wide. Presence of Persistent Subtending Bract (Palea): Present. Bract Length: 2 cm, with 5 mm long hairs at base. Bract Tip Color: RHS 163A. Bract Middle Color: RHS 144A. Bract Base Color: RHS 159D. Number of Lobes of Corollas: Entire to 4. Corolla Length: 1.75-2.25 cm. Corolla Width: 4-9 mm. Base Shape: Tubular. Lobes: Spreading, fan shaped to tubular. Texture Outside: Tip: Smooth. Base: Smooth. Texture Inside: Tip: Smooth. Base: Smooth. Outside Color: Tip: Immature RHS 10B maturing to RHS 153B. Base: Immature RHS 154D maturing to RHS 153C. Inside Color: Tip: Immature color RHS 13B maturing closest to RHS 15A. Base: RHS 150B maturing to RHS15D. Pistil Length: 8 mm. Ovary Length: 2.5 mm. Ovary Color: RHS NN155A. Style Length: 5 mm. Style Color: RHS 145B at tip, closest to RHS 136D at base. Stigma Length: 0.5 mm. Stigma Branched or Not: Branched and curling. Stigma Branching Spread: 1.0-1.5 mm. Stigma Color: RHS 17A, aging to RHS 166B. Stamen Length: 5 mm. Anther Length: 2 mm. Anther Color: Between RHS 197C and RHS 197D, aging to RHS 166B. Filament Length: 3 mm. Filament Color: Closest to RHS 196D, oxidizes quickly. Pollen Present: Yes. Pollen Color: RHS 13C.

Involucral bracts:

*In 4 leafy series*.—Area grows to 3.5 cm wide and 13 mm deep.

*Lobe shape*.—Lanceolate.

*Lobes reflexed*.—Yes.

*Lobe length*.—Up to 14 mm.

*Lobe width*.—4 mm.

*Lobe color*.—Closest to RHS 146A.

*Lobe margins*.—Entire, strigose.

*Lobe tip*.—Acute.

*Lobe surface texture*.—Strigose.

Receptacle:

*Size*.—Grows to 12 mm wide at base and 25 mm tall.

*Color*.—RHS NN155D, oxidizes quickly.

Bloom period: June though October in Canby, OR.

Fragrance: Strong, very sweet and pleasant, honey-like.

Inflorescence lastingness: About 2 weeks.

Seed:

*Shape*.—Oval.

*Size*.—3-4 mm long, 2 mm wide.

*Color*.—RHS N200A.

*Fertility*.—Poor.

I claim:

1. A new and distinct variety of *Echinacea* plant named 'Fried Egg', substantially as illustrated and described herein.

* * * * *